(12) United States Patent
Oda (10) Patent No.: US 11,938,254 B2
(45) Date of Patent: Mar. 26, 2024

(54) HOLLOW FIBER MEMBRANE-TYPE ARTIFICIAL LUNG

(71) Applicant: NATIONAL UNIVERSITY CORPORATION SHIMANE UNIVERSITY, Matsue (JP)

(72) Inventor: Teiji Oda, Izumo (JP)

(73) Assignee: NATIONAL UNIVERSITY CORPORATION SHIMANE UNIVERSITY, Matsue (JP)

( * ) Notice: Subject to any disclaimer, the term of this patent is extended or adjusted under 35 U.S.C. 154(b) by 697 days.

(21) Appl. No.: 17/040,936

(22) PCT Filed: Mar. 26, 2019

(86) PCT No.: PCT/JP2019/012655
§ 371 (c)(1),
(2) Date: Sep. 23, 2020

(87) PCT Pub. No.: WO2019/189055
PCT Pub. Date: Oct. 3, 2019

(65) Prior Publication Data
US 2021/0015985 A1    Jan. 21, 2021

(30) Foreign Application Priority Data
Mar. 26, 2018    (JP) ................. 2018-057727

(51) Int. Cl.
 *A61M 1/16*    (2006.01)
 *B01D 69/08*    (2006.01)
 *A61M 1/36*    (2006.01)

(52) U.S. Cl.
CPC ........ *A61M 1/1698* (2013.01); *A61M 1/1627* (2014.02); *A61M 1/1629* (2014.02);
(Continued)

(58) Field of Classification Search
CPC ............. A61M 1/1698; A61M 1/1627; A61M 1/1629; A61M 1/1664; A61M 2202/0208;
(Continued)

(56) References Cited

U.S. PATENT DOCUMENTS 3,927,981 A    12/1975    Viannay et al.
4,599,093 A    7/1986    Steg, Jr.
(Continued)

FOREIGN PATENT DOCUMENTS

DE    3142751 A1    6/1982
JP    H11-206880 A    8/1999
(Continued)

OTHER PUBLICATIONS

German Patent and Trade Mark Office, Office Action in German Patent Application No. 11 2019 001 632.6 (dated Jan. 25, 2023).
(Continued)

*Primary Examiner* — Philip R Wiest
(74) *Attorney, Agent, or Firm* — Leydig, Voit & Mayer, Ltd.

(57) ABSTRACT

The present invention provides a hollow fiber membrane oxygenator comprising
 a housing comprising a blood flow path;
 a blood inlet port and a blood outlet port disposed in the housing so as to allow blood to flow through the blood flow path;
 a gas exchange part comprising a bundle of a plurality of hollow fiber membranes disposed in the blood flow path,
 a gas inflow port and a gas outflow port provided in the housing so as to allow an oxygen-containing gas to flow through lumens of the hollow fiber membranes, and
(Continued)

a gas temperature control part for adjusting the temperature of a gas flowing through the lumens of the hollow fiber membranes.

8 Claims, 9 Drawing Sheets

(52) U.S. Cl.
CPC ........... *A61M 1/1664* (2014.02); *B01D 69/08* (2013.01); *A61M 1/3623* (2022.05); *A61M 2202/0208* (2013.01); *A61M 2202/025* (2013.01); *A61M 2205/366* (2013.01)

(58) Field of Classification Search
CPC ...... A61M 2202/025; A61M 2205/366; B01D 69/08
See application file for complete search history.

(56) References Cited

U.S. PATENT DOCUMENTS

| | | | | | |
|---|---|---|---|---|---|
| 5,137,531 | A | * | 8/1992 | Lee | B01D 63/04 422/46 |
| 5,225,161 | A | * | 7/1993 | Mathewson | A61M 1/1698 165/182 |
| 2009/0180324 | A1 | * | 7/2009 | Ramaswamy | H10B 43/35 438/129 |
| 2010/0114004 | A1 | * | 5/2010 | Tanaka | B01D 63/02 604/6.13 |
| 2010/0290947 | A1 | * | 11/2010 | Nakao | A61M 1/1629 422/46 |
| 2012/0063953 | A1 | * | 3/2012 | Izumida | A61M 1/1698 165/173 |

FOREIGN PATENT DOCUMENTS

| | | |
|---|---|---|
| JP | 2000-005302 A | 1/2000 |
| JP | 2001-170169 A | 6/2001 |
| JP | 5674456 B2 | 2/2015 |
| JP | 2017-136198 A | 8/2017 |

OTHER PUBLICATIONS

Japanese Patent Office, International Search Report in International Patent Application No. PCT/JP2019/012655 (dated May 14, 2019).

* cited by examiner

HOLLOW FIBER MEMBRANE-TYPE ARTIFICIAL LUNG

CROSS-REFERENCE TO RELATED APPLICATIONS

This patent application is the U.S. national phase of International Patent Application No. PCT/JP2019/012655, filed Mar. 26, 2019, which claims the benefit of Japanese Patent Application No. 2018-057727, filed Mar. 26, 2018, which are incorporated by reference in their entireties herein.

TECHNICAL FIELD

The present invention relates to a hollow fiber membrane oxygenator that performs gas exchange for blood in extracorporeal circulation.

BACKGROUND ART

In an artificial lung (extracapillary blood flow type hollow fiber membrane oxygenator), oxygen-containing gas flowing inside of hollow fibers passes through hollow fiber membranes to provide oxygen to the blood flowing outside of the membranes; whereas carbon dioxide in the blood moves in the opposite direction into the hollow fibers, thus achieving a gas exchange function equivalent to that of lungs (Patent Literature (PTL) 1). However, when blood components, such as cells, proteins, and small molecules, come into contact with hollow fiber membranes having a surface area of 1.3 to 2.3 $m^2$, the membranes are recognized as a foreign substance and the biological defense system is activated (acute inflammatory response); this may spread throughout the body and cause a systemic acute inflammatory response, thus leading to complications, such as critical organ damage. This remains a major clinical problem today.

To solve this problem, a method of coating the surface of hollow fiber membranes with heparin or a polymer to inhibit the activation of blood components has been applied to almost all oxygenators. However, the problem has yet to be adequately resolved.

There is another problem in that during gas exchange through the hollow fiber membranes of an oxygenator, water vapor that moves from the blood into hollow fibers dew-condenses in the vicinity of the outlet of the hollow fibers, which increases the resistance to gas flow. Although the generation of dew-condensed water can be reduced by heating the area of the outlet of the hollow fibers, the condensed water has been a problem in terms of the management of oxygenators.

CITATION LIST

Patent Literature

PTL 1: JP2017-136198A

SUMMARY OF INVENTION

Technical Problem

An object of the present invention is to reduce acute inflammatory response and complications caused by the use of an oxygenator.

Another object of the present invention is to provide a means of efficiently controlling the blood temperature.

Another object of the present invention is to inhibit dew condensation in an oxygenator.

Another object of the present invention is to perform rapid whole-body cooling by perfusion of a small amount of cold water.

Solution to Problem

The present invention provides the following hollow fiber membrane oxygenators.

Item 1.
　A hollow fiber membrane oxygenator comprising
　a housing comprising a blood flow path;
　a blood inlet port and a blood outlet port disposed in the housing so as to allow blood to flow through the blood flow path;
　a gas exchange part comprising a bundle of a plurality of hollow fiber membranes disposed in the blood flow path,
　a gas inflow port and a gas outflow port provided in the housing so as to allow an oxygen-containing gas to flow through lumens of the hollow fiber membranes, and
　a gas temperature control part for adjusting the temperature of the gas flowing through the lumens of the hollow fiber membranes.

Item 2.
　The hollow fiber membrane oxygenator according to Item 1, wherein the oxygen-containing gas further contains helium gas.

Item 3.
　The hollow fiber membrane oxygenator according to Item 1 or 2, wherein the gas temperature control part comprises cold- or warm-water flow pipes.

Item 4.
　The hollow fiber membrane orygenator according to Item 1 or 2, wherein the gas temperature control part comprises rod-shaped members disposed in hollow fibers, and cooling mechanisms for cooling the rod-shaped members.

Item 5.
　The hollow fiber membrane oxygenator according to any one of Items 1 to 4, wherein the hollow fiber membranes and the gas temperature control part constitute a heat exchange part, and the oxygenator is a hollow fiber membrane-based gas and heat exchanger.

Item 6.
　The hollow fiber membrane orygenator according to Item 2, further comprising a gas separation membrane for recovering helium from gas released from the gas outflow port.

Advantageous Effects of Invention

According to the hollow fiber membrane oxygenator of the present invention, blood inflammatory response and the risk of complications can be reduced by temperature-controlled gas passing inside of hollow fibers.

When saturated water vapor in hollow fibers that are humidified and warmed by the blood is rapidly cooled in the vicinity of the gas outlet, condensation (dew-condensation) can occur. However, since the hollow fiber membrane oxygenator according to the present invention significantly inhibits the condensation as compared with conventional oxygenators, the burden of maintaining and managing the oxygenator is reduced, and durability is improved.

Further, the oxygenator of the present invention has excellent blood-cooling efficiency and improved oxygenator gas exchange (oxygenation).

Further, the oxygenator of the present invention is capable of rapid whole-body cooling by perfusion of a small amount of cold water, and is capable of inducing rapid whole-body cooling and the resulting suspended animation. Therefore, the application of the oxygenator of the present invention is expected to be extended to organ donation after cardiac death, severe trauma, sudden death.

DESCRIPTION OF EMBODIMENTS

Figure 5:
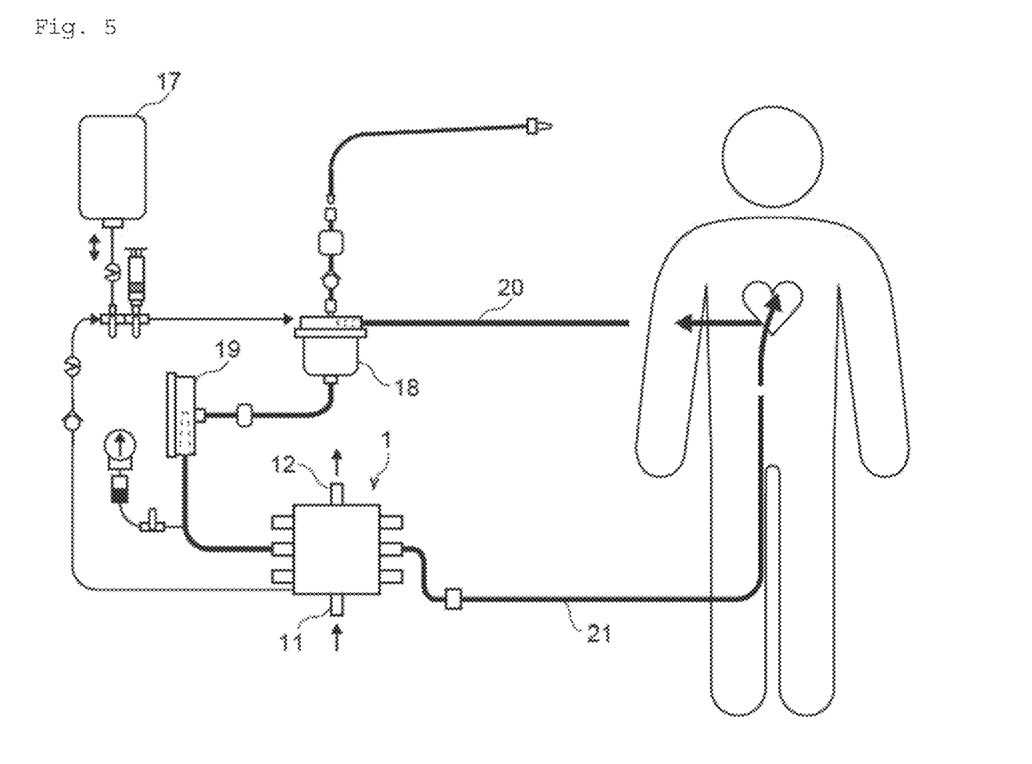
FIG. 5 shows an example of a cardiopulmonary bypass circuit.

The artificial cardiopulmonary circuit used in cardiac surgery comprises various devices and circuits for assisting surgery (see, for example, FIG. 5). In FIG. 5, 17 is a volume adjustment bag, 18 is a vented arterial filter, 19 is a centrifugal pump, 20 is a blood discharge line, and 21 is a blood supply line.

In one preferred embodiment of the present invention, the hollow fiber membrane oxygenator, which comprises hollow fiber membranes having a large surface area, has the largest contact area with blood, and accounts for 80 to 90% of the total surface area of the artificial materials of the cardiopulmonary bypass circuit in contact with the blood. Accordingly, improving the biocompatibility of the oxygenator provides the greatest effect.

In the ECMO (extracorporeal membrane oxygenation) and ECLS (extracorporeal life support), which are new methods of utilizing an oxygenator, the system is composed of an orygenator, a pump, and tubes. Therefore, the importance of the oxygenator further increases. The hollow fiber membrane oxygenator of the present invention is preferably used for heart-lung machine, ECMO, and ECLS. ECMO life support for pandemic influenza plays an important role in saving the lives of patients with severe respiratory failure.

Furthermore, the hollow fiber membrane oxygenator of the present invention can be applied to organ donation after cardiac death, severe trauma and sudden death.

A feature of the hollow fiber membrane oxygenator of the present invention is that the orygenator comprises a gas temperature control part for adjusting the temperature of oxygen-containing gas flowing inside of the hollow fiber membranes. The temperature control is cooling at the start of or during the use of the oxygenator. For local cooling, rewarming the blood is not always necessary; however, for whole-body cooling, blood is preferably rewarmed (the blood temperature is raised) before removing the cardiopulmonary bypass. The oxygen-containing gas is always maintained in a state temperature-controlled by the gas temperature control part. When the oxygen-containing gas flowing inside of the hollow fiber membranes is released to the outside from the pores of the hollow fiber membranes and comes into contact with the blood, the blood comes into contact with the temperature-controlled (particularly cooled) oxygen-containing gas; accordingly, acute inflammatory response, blood coagulation reactions, and the like caused by the contact with foreign matter (hollow fiber membranes) are inhibited.

The hollow fiber membrane oxygenator of the present invention has a very high blood-cooling capacity, and thus can be used as a heat exchanger for rapidly cooling blood. When the hollow fiber membrane oxygenator of the present invention is used as a heat exchanger, a helium-containing gas can be circulated in the lumens of the hollow fiber membranes. Alternatively, a gas consisting of helium may be circulated. 100% helium has a thermal conductivity (W/m/K) of 0.1442 W/m/K; a mixed gas of 50% oxygen and 50% helium has a thermal conductivity of 0.036378 W/m/K; and a mixed gas of 50% oxygen and 50% nitrogen has a thermal conductivity of 0.024393 W/m/K. When the purpose is cooling the blood, helium gas is the most preferable. When helium gas is used for the purpose of cooling the blood, flowing helium together with a small amount of a gas known to have a protective effect against ischemia-reperfusion injury, such as carbon monoxide (CO), nitric oxide (NO), hydrogen sulfide or its analogues (hydrogen sulfide=$H_2S$; hydrogen selenide=$H_2Se$), or hydrogen may possibly further increase the effect of the rapid-cooling method.

In a preferred embodiment of the present invention, one feature of the present invention is "improvement in the biocompatibility of an oxygenator (inflammatory response and thrombosis inhibition) by prevention of dew-condensation via controlling gas temperature in the oxygenator and local cooling" in a pathological condition (ARDS) that requires a long-term (2 to 4 weeks) life support (ECMO) therapy with a membrane oxygenator. This effect can reduce the number of exchanges of the oxygenator during ECMO treatment, and diminish the deterioration of the original serious disease state caused by the ECMO-induced systemic inflammatory response. In this case, the membrane oxygenator of the present invention, which uses local blood-cooling, does not cause side effects. The whole-body cooling may possibly cause complications in a hypothermic state. The membrane oxygenator of the present invention can avoid the complications. The rapid-cooling method using the membrane oxygenator of the present invention is preferably applied to life-threatening critical conditions.

It has been a common practice that when an oxygenator is used, whole-body cooling is performed to inhibit inflammatory response, blood coagulation reactions, and the like.

However, whole-body cooling has been reported to have the following side effects:
1) since the immune system is inhibited, infectious diseases, such as pneumonia, increase;
2) due to functional deterioration of platelets and coagulation factors, blood coagulation function is reduced, thus increasing bleeding complications; hemostasis is difficult to achieve during surgery, resulting in increased blood loss and prolonged operation time; and
3) if hypothermia progresses, arrhythmias and hypotension occur (Table 1).

TABLE 1

Side effects of hypothermia

| Side effects | Sequelae | References |
|---|---|---|
| Shivering | Worsening of heart disease in the elderly with heart disease | 1) Frank SM et al. JAMA 1997; 277: 1127-1134. 2) Frank SM, et al., Anesthesiology 1993; 78: 468-476. 3) Leslie K, et al., Best Pract Res Clini Anaesthesiology 1993; 17: 485-498. |
| Metabolism inhibition (8% decrease per 1° C.) | | Polderman KH, Grit Care 2009; 37 (SupplI): S186-S202 |
| Reduced insulin sensitivity, and reduced insulin secretion | Hyperglycemia | Polderman KH, Crit Care 2009; 37 (SupplI): S186-S202 |
| Decrease of magnesium, potassium, and phosphate (when cooled); and increase of magnesium, potassium, and phosphate (when rewarmed) | Arrhythmia; infection | 1) Polderman KH, et al., J Neurosurg 2001; 94: 697-705, 2) Weisinger JR, et al., Lancet 1998; 352: 391-396 |
| Reduced heart rate, hypotension, decreased cardiac function, decrease in circulating blood volume | Circulatory failure | Polderman KH, Crit Care 2009; 37 (SupplI): S186-S202 |
| ECG abnormality (prolonged PR interval, widening of QRS width, appearance of Osborn waves) | | 1) Polderman KH, Crit Care 2009; 37 (SupplI): S186-S202. 2) Higuchi S, et al., Circ J 2014; 78: 128-134. |
| Severe arrhythmia (atrial fibrillation, ventricular tachycardia, ventricular fibrillation) | Death | Polderman KH, Crit Care 2009; 37(SupplI): S186-S202 |
| Blood coagulation disorders: thrombocytopenia (33° C. or less), platelet function disorders (35° C. or less), coagulation factor disorders (33° C. or less) | Bleeding (complications in hemostasis) | 1) Polderman KH, et al. Crit Care Med 2009; 37: 1101-1120. 2) Staikou C, et al, J Surg Res 2011; 167: 125-130. |
| Leukocyte migration, decreased phagocytosis, decreased cytokine secretion | Increased susceptibility to infection | 1) Polderman KH, et al., Crit Care Med 2009; 37: 1101-1120, 2) Kurz A, et al., N Engl J Med 1996; 334: 1209-1215, 3) Peterson K, et al., J Neurotrauma 2008; 25: 62-71, 4) Schwab S, et al., Stroke 2001; 32: 2033-2035. |
| Decreased gastrointestinal motility | | Polderman KH, Crit Care 2003; 37 (SupplI): S186-S202 |

The whole-body cooling method has other drawbacks:

4) Whole-body cooling takes a longer time than cooling only the oxygenator. Although it depends on the target temperature, whole-body cooling takes about 30 minutes, during which a full effect cannot be obtained. Because of the above problems, the method of cooling only the heart, rather than whole-body hypothermia (cooling), is more prevalent in cardiac surgery; and the level of hypothermia tends to be set higher.

5) Whole-body cooling requires a large device (a cold- or warm-water tank), and a heart exchange water flow rate of 10 to 15 L/min between the cold- or warm-water tank and the heat exchanger built into the oxygenator connected thereto. This does not pose a significant difficulty in operating room cardiac surgery. However, in the case of ECLS/ECMO used for resuscitation of severe respiratory failure or cardiopulmonary arrest, it is a significant burden on medical staff because it is used in an intensive care unit, emergency room, or at the scene of cardiopulmonary resuscitation.

In contrast, the hollow fiber membrane oxygenator of the present invention selectively cools the local area inside the oxygenator where the blood and hollow fiber membranes come into contact with each other. Accordingly, the reaction of the blood to the oxygenator (biological defense response) can be controlled without affecting the whole body, thus resulting in no occurrence of the side effects described above in items 1) to 3) described in [0024]

Furthermore, since immediate cooling is achieved and the required heat exchange water flow rate is about 1 to 2 L/min, the cold- or warm-water tank can be significantly downsized, and the problems described above in 4) and 5) do not occur.

The present inventors performed a rapid blood-cooling test using an oxygenator manufactured by Terumo Corporation (trade name: Terumo CAPIOX FX15) and a double-pipe oxygenator of the present invention shown in FIG. 1, by the experimental method described below and shown in FIG. 9.

Figure 9:
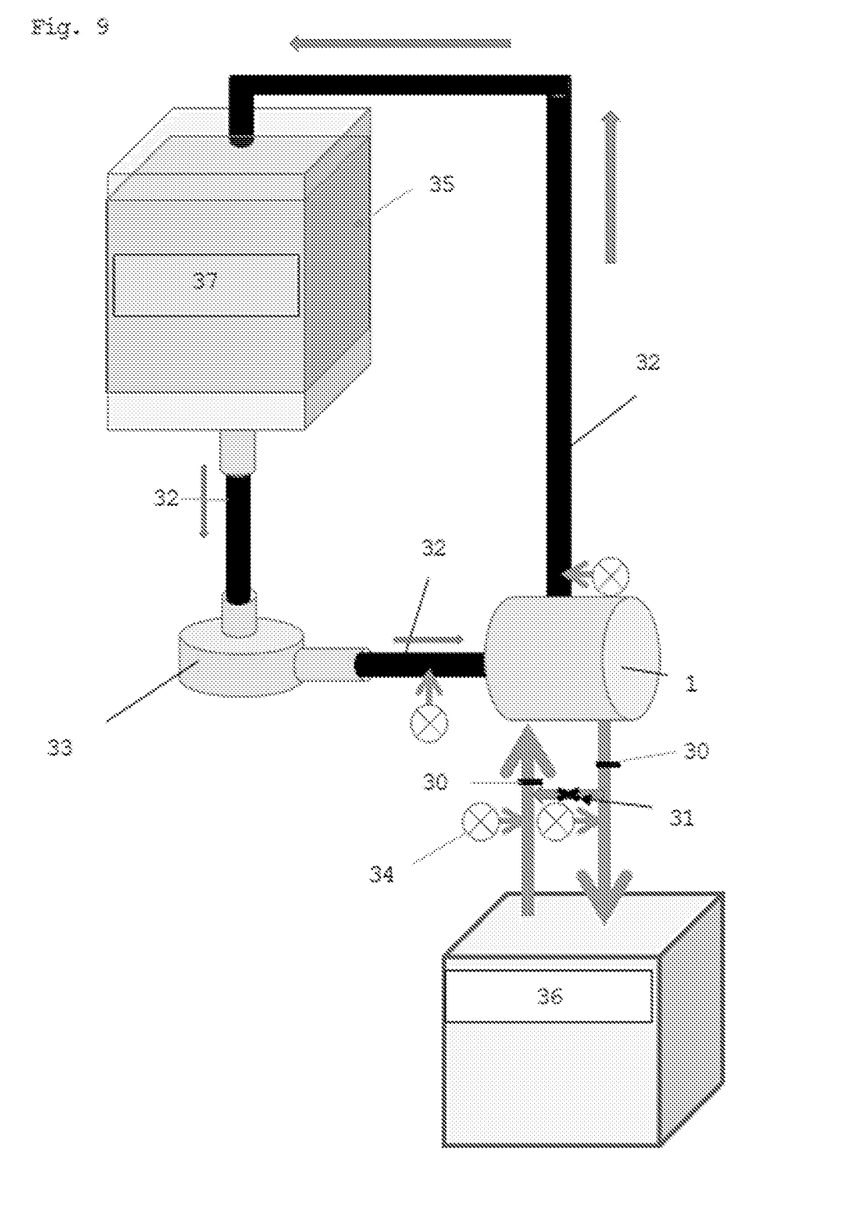
FIG. 9 shows an apparatus used in a rapid-cooling test.

Methods: a circuit is prepared using a centrifugal pump (33) (perfusion at 4 L/min), an oxygenator (1), and a venous reservoir (37) to circulate heated saline (3L). For example, the connection portion between a cold- or warm-water tank (36) and the oxygenator (1) is first blocked with two-way cocks (30) to create a closed circuit, and the cold- or warm-water tank (36) is cooled to 4° C. At the same time as the start of the cooling test, the blockage with the two-way cocks (30) is released and the flow is blocked with a two-way valve (31) to perform a rapid-cooling test via the oxygenator (1) (heat exchange part).

Table 2 shows the results. In Table 2, "%" indicates "capacity %."

TABLE 2

| Oxygenator | Cooling experiment conditions | Cooling rate | Perfusion, rate in the cold- or warm-water tank (4° C.) |
|---|---|---|---|
| Terumo oxygenator Test 1 | 33.9° C. → 20.7° C./14 sec | 0.94° C./sec | 12 L/min |
| Terumo oxygenator Test 2 | 34.2° C. → 23.0° C./12 sec | 0.93° C./sec | 12 L/min |
| Double-pipe membrane oxygenator of the present invention, He 50% + $O_2$ 50% | 35.0° C. → 29.2° C./2.1 sec | 2.76° C./sec | 1 L/min |
| Double-pipe membrane oxygenator of the present invention, He 100% | 35.0° C. → 27.3° C./2.1 sec | 3.67° C./sec | 1 L/min |

TABLE 2-continued

| Oxygenator | Cooling experiment conditions | Cooling rate | Perfusion, rate in the cold- or warm-water tank (4° C.) |
|---|---|---|---|
| Double-pipe membrane oxygenator of the present invention, He 50% + O$_2$ 50% | 35.0° C. → 27.5° C./2.1 sec | 3.57° C./sec | 2 L/min |

Although the oxygenator of the present invention requires a lower cold- or warm-water perfusion rate (1 liter or 2 liters per minutes) than the commercially available orygenator manufactured by Terumo Corporation (12 liters per minute), the cooling rate achieved by the oxygenator of the present invention is about 3 to 4 times higher. The results clearly show that the oxygenator of the present invention is capable of rapid whole-body cooling via blood-cooling, and that downsizing of the cold- or warm-water tank can be achieved due to its lower cold- or warm-water perfusion rate. Since downsizing of the cold- or warm-water tank can be achieved, the system of ECLS/ECMO including the oxygenator of the present invention can be installed in an ambulance.

In a preferred embodiment of the present invention, the gas flowing through the orygenator is controlled by an oxygen monitor (degree of oxygen saturation) disposed on the biological side; 100% helium is allowed to flow at an oxygen saturation of >90%, whereas 50% oxygen and 50% helium gas are allowed to flow at an oxygen saturation of <90%, whereby gas exchange and heat exchange can both be achieved; furthermore, extremely rapid whole-body cooling/heating can be achieved, as compared to conventional oxygenators. Therefore, the orygenator of the present invention also functions as a hollow fiber membrane gas and heat exchanger. To enhance safety, the degree of oxygen saturation of brain tissue can be monitored by using a near-infrared tissue oxygen saturation monitor (e.g., INVOS, manufactured by Covidien Japan; Fore-Sight, manufactured by Century Medical Inc.), and used as an indicator of adequate oxygenation.

The material of the hollow fiber membranes is not particularly limited. The same materials as those of hollow fiber membranes used in conventional oxygenators can be used. Examples include silicone (a homogeneous membrane), polypropylene (a porous membrane), polymethylpentene (an asymmetric membrane), silicone coating (a composite film), and the like. The inner diameter of the hollow fiber membranes is not particularly limited, but is preferably 50 to 900 µm. The outer diameter of the hollow fiber membranes is not particularly limited, but is preferably 100 to 1000 µm. The thickness of the hollow fiber membranes is not particularly limited, but is preferably 20 µm to 100 µm.

An embodiment of the present invention is described with reference to drawings.

Figure 1:
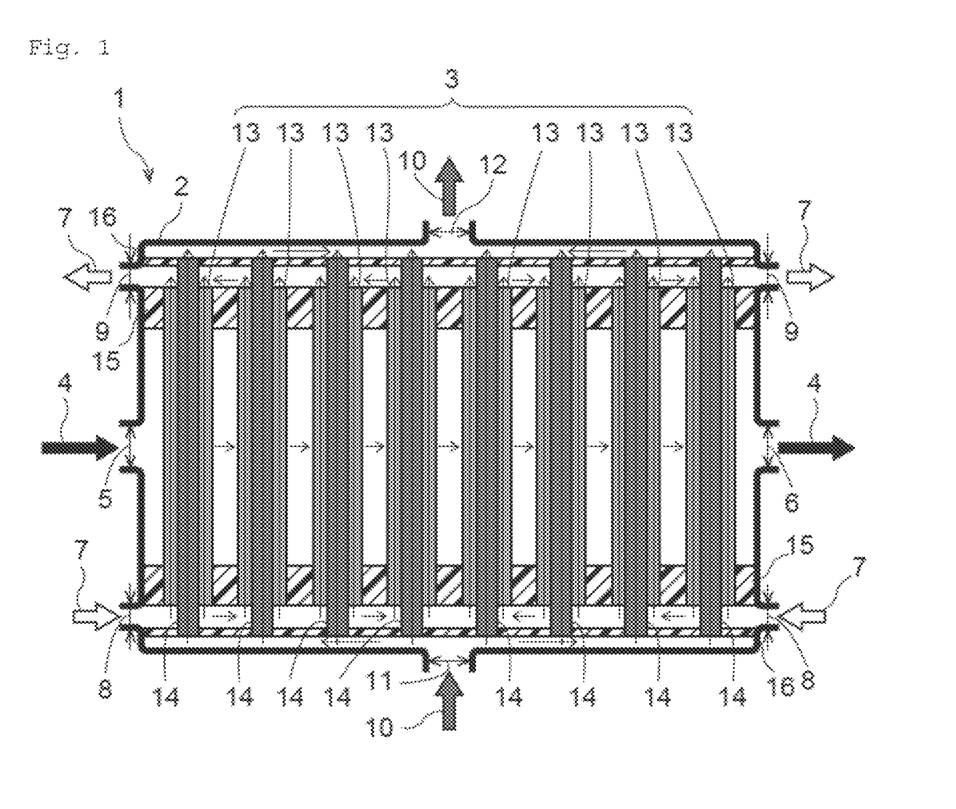
FIG. 1 is a cross-sectional view of the hollow fiber membrane oxygenator of the present invention comprising a gas exchange part comprising a bundle of a plurality of hollow fiber membranes.

FIG. 1 is a cross-sectional view schematically showing the hollow fiber membrane oxygenator 1 of the present invention. This oxygenator 1 has a gas exchange part 3 built into the housing 2. The housing 2 comprises a blood inlet port 5, a blood outlet port 6, a gas inflow port 8, a gas outflow port 9, a medium inlet port 11, and a medium outlet port 12. The oxygenator may have any shape. Examples of shapes include, but are not limited to, cylindrical, elliptic cylindrical, rectangular cylindrical, and like shapes.

In one preferred embodiment of the present invention, the hollow fiber membrane oxygenator of the present invention further comprises a gas separation membrane (not shown) for recovering helium from the gas discharged from the gas outflow port 9. The helium gas separated by the gas separation membrane can be reused.

The blood 4 flows into the gas exchange part 3 through the blood inlet port 5, passes between the hollow fiber membranes 13, flows out of the blood outlet port 6, and is sent to a blood supply circuit (arterial line). The gas exchange part 3 comprises a plurality bundle of hollow fiber membranes 13, and a temperature control pipe 14 is disposed as a gas temperature control part 14 in each hollow fiber membrane 13. When cold water flows as a medium through the temperature control pipe 14, the pipe serves as a cooling pipe 14; whereas when warm water is allowed to flow for re-warming, the pipe serves as a warm-water pipe 14. The temperature of water that flows through the temperature control pipe is preferably 4 to 42° C., more preferably 4 to 38° C. The temperature for cooling the blood is preferably 4 to 36° C., and the temperature for rewarming the blood is preferably 36 to 38° C.

It is important to change the setting temperature of the cold or warm water flowing through the temperature control pipe in accordance with the patient's condition. For example, during ECMO treatment, if the patient has a pathological condition in which blood clots frequently form in the oxygenator despite anticoagulation therapy, the water should be set at a lower temperature that strongly inhibits blood coagulation. If a patient has a pathological condition in which gas exchange in the oxygenator deteriorates quickly and frequent replacement of the oxygenator is required, which is deemed to be caused by dew-condensation in the hollow fibers, countermeasures are necessary. For example, the water should be set at a temperature that strongly inhibits condensation of water vapor (35° C. to blood temperature; no cooling); the proportion of helium gas should be increased; or the amounts of gas and water should be increased.

The upper and lower ends of each hollow fiber membrane 13 are fixed by partition walls 15, and the upper and lower ends of each temperature control pipe are fixed by partition walls 16. A flow path for the oxygen-containing gas 7 is between the partition walls 15, 16. A flow path for the medium 10, such as cold water or warm water, is between the housing 2 and the partition walls 16. The oxygen-containing gas 7 flows in from the gas inflow port 8 and passes through the hollow fiber membranes 13 for gas exchange with the blood 4, takes carbon dioxide from the blood, and releases oxygen into the blood. The oxygen-containing gas whose oxygen concentration has decreased and whose carbon dioxide concentration has increased due to gas exchange flows out of the gas outflow port 9. The medium 10 is pumped in from the medium inlet port 11, passes through the temperature control pipe 14, and flows out of the medium outlet port 12. The oxygen-containing gas 7 in contact with the temperature control pipe 14 is controlled in temperature (for example, cooled) by allowing the medium 10 to flow through the temperature control pipe 14. When the oxygenator is applied, the oxygen-containing gas 7 that comes into contact with the blood through pores of the hollow fiber membranes 13 is cooled to a temperature sufficiently lower than the temperature of the blood 4, to thereby inhibit inflammatory response or the like during gas exchange with the blood.

The present inventors investigated sending cooled gas into hollow fiber membranes without using a cold-water pipe. The inventors found that the use of cooling gas alone could not cool hollow fiber membranes and the vicinities thereof due to the small heat capacity of the gas, and thus could not sufficiently inhibit inflammatory response and the like during gas exchange. On the other hand, the use of cold-water pipe 14 could sufficiently cool the hollow fiber membranes and the vicinities thereof, and thus could inhibit inflammatory response and the like during the gas exchange with the blood.

Figure 6:
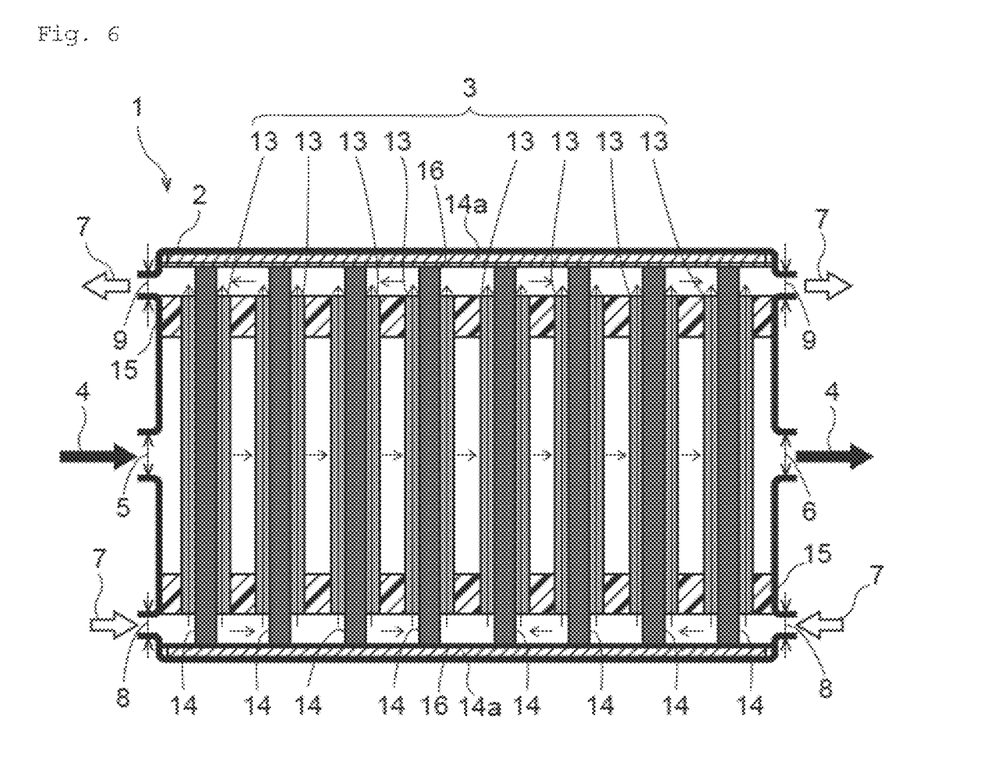
FIG. 6 is a cross-sectional view of another embodiment of the hollow fiber oxygenator of the present invention.

When hollow temperature control pipes 14 are used as the gas temperature control part 14 of the present invention, the oxygen-containing gas 7 can be cooled by allowing a medium 10, such as cold water or warm water, to flow through the temperature control pipes 14. However, when solid thermally conductive metal wires 14 (in the form of a rod or wire) are used as the gas temperature control part 14, and a metal partition wall 16 and all the metal wires 14 are cooled or heated by a temperature control unit 14a attached to the partition wall 16, the thermally conductive metal wires 14 can be cooled or heated without using cold water or warm water (medium) 10 (FIG. 6). The material of the wires is preferably a metal having high thermal conductivity (e.g., stainless steel); however, any non-metal materials can also be used, as long as they can cool the gas. When the blood is to be rewarmed, rewarming can be achieved by heating the thermally conductive wires 14.

The temperature control unit 14a is preferably a small Peltier temperature control unit. Alternatively, the temperature control unit 14a can be a temperature control unit using a refrigerant, such as a vapor compression refrigeration cycle, an absorption refrigeration cycle, or an air refrigeration cycle; or a magnetic refrigeration system temperature control unit without using a refrigerant. Alternatively, when cooling the blood, the gas temperature control part can be cooled by using a refrigerant such as dry ice. When a magnetic refrigeration system temperature control unit is used, wires are composed of a material comprising a magnetic material.

The oxygen-containing gas 7 may be 100% oxygen gas, or may contain an inert gas, such as nitrogen, helium, or argon. The oxygen-containing gas 7 is preferably a gas containing oxygen and helium. Helium is preferred because of its high thermal conductivity. When a mixed gas of helium and oxygen is used, the gas is preferably a mixed gas comprising 20 to 100 volume % of oxygen and 0 to 100 volume % of helium, and more preferably a mixed gas comprising 20 to 50 volume % of oxygen and 50 to 80 volume % of helium.

The present inventors microscopically observed the hollow fiber membranes of the oxygenator of the present invention in a state in which cooling with water (4° C.) was not performed in the gas temperature control part 14. Slightly coagulated blood was found to adhere to the surface of the hollow fiber membranes. On the other hand, no blood coagulation was observed in the hollow fiber membranes of the oxygenator of the present invention when cooling with water (4° C.) in the gas temperature control part 14. This indicates that the oxygenator 1 of the present invention is highly effective in inhibiting blood coagulation.

Many research papers have shown that blood coagulation is inhibited even when blood temperature is lowered by only 2 to 3° C. (to 32 to 35° C.). Setting the blood temperature at 32 to 35° C., which is a condition in which the amount of water vapor condensation is inhibited, can possibly inhibit blood clotting, and also strongly inhibit water vapor condensation at the same time.

Figure 2:
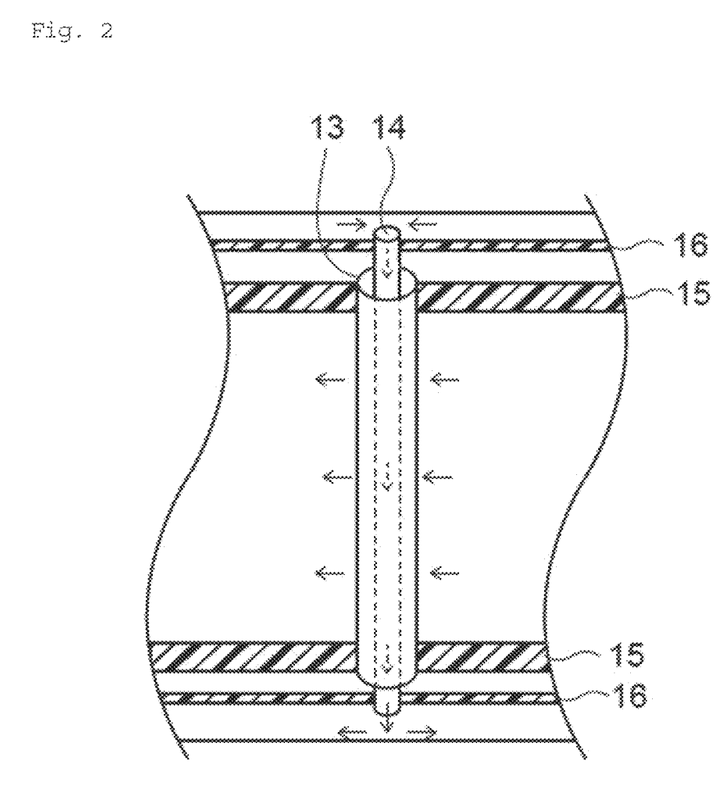
FIG. 2 shows one embodiment of the gas temperature control part.

FIG. 2 shows one embodiment of the gas temperature control part, wherein the gas temperature control part 14 is a temperature control pipe 14 through which cold water flows.

Figure 3:
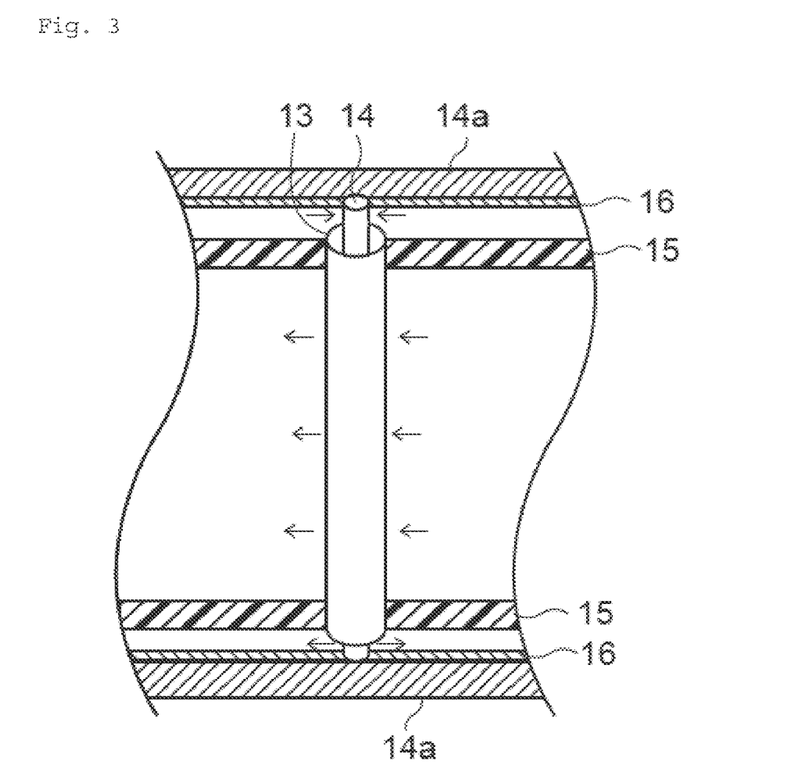
FIG. 3 shows another embodiment of the gas temperature control part.

FIG. 3 shows another embodiment of the gas temperature control part, wherein the gas temperature control part 14 comprises a metal wire 14, such as a wire made of stainless steel, a metal partition wall 16, and a Peltier cooling unit 14a for cooling these components.

Figure 4:
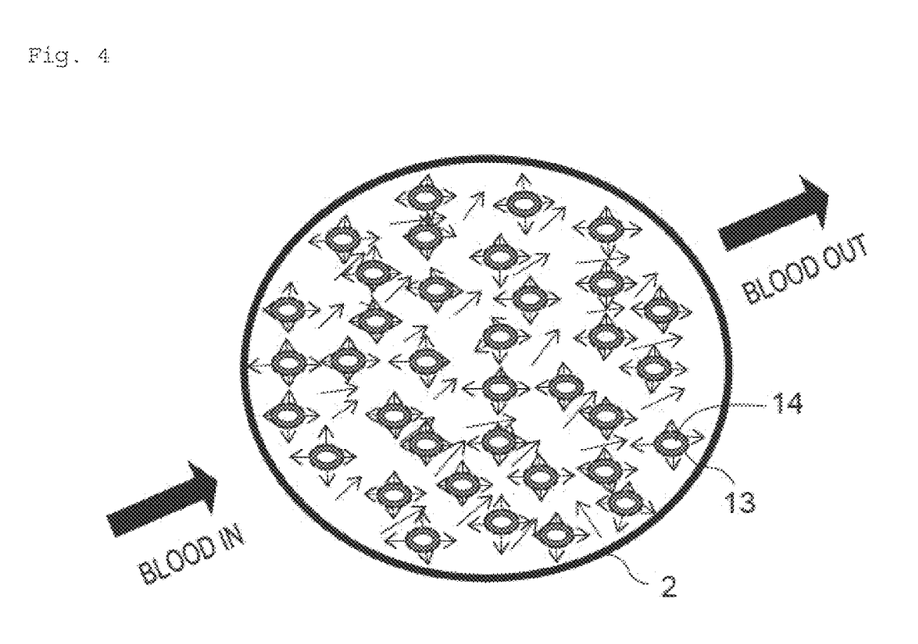
FIG. 4 shows the state of hollow fiber membranes in the oxygenator.

FIG. 4 is a cross-sectional schematic diagram of the membrane cooling oxygenator of the present invention, wherein many hollow fiber membranes 13 are disposed in an oval-shaped housing 2, and the blood flows between the hollow fiber membranes 13 in the direction of the arrows. Further, temperature control pipes 14 are disposed inside the hollow fiber membranes 13, and cold water is allowed to flow in the temperature control pipes 14 to thereby cool the gas flowing in the hollow fiber membranes 13. The cooled gas flows through the pores of the hollow fiber membranes 13 in the directions of arrows to thereby cool the blood flowing between the hollow fiber membranes 13.

Figure 7:
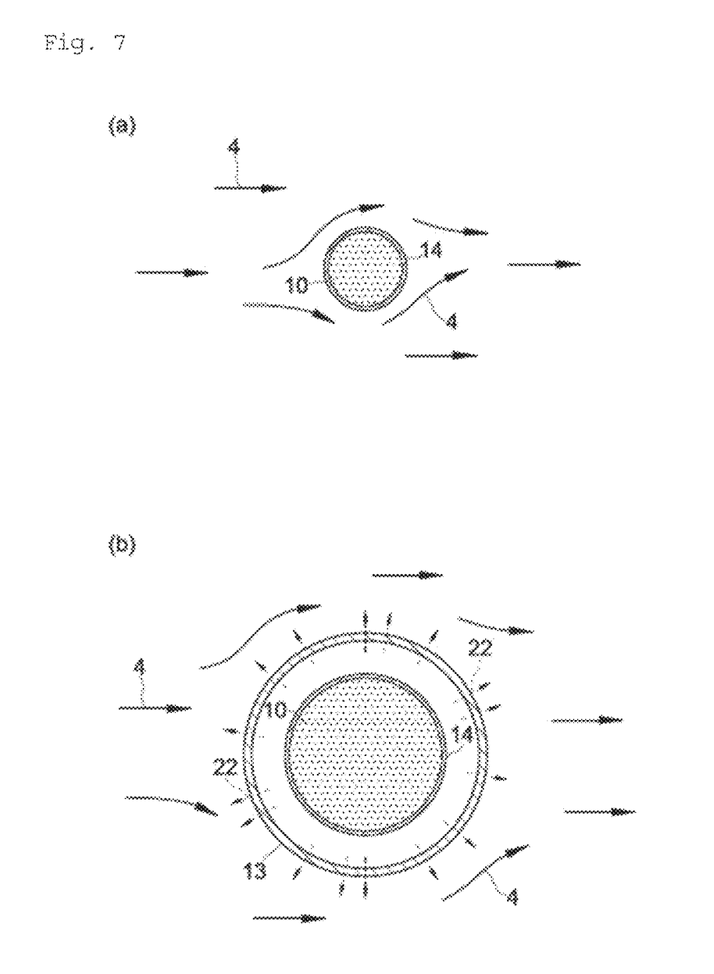
FIG. 7(a) is a cross-sectional view of a conventional heat exchange cooling pipe.
FIG. 7(b) is a cross-sectional view of the gas temperature control part of the present invention.

FIG. 7 schematically illustrates a conventional heat exchange pipe (a) and the double-pipe oxygenator (b) of the present invention. The oxygenator of the present invention cools the blood by using cooling gas 22 (in particular, He+$O_2$), whereby it can cool the blood much more efficiently than using a metal heat exchanger pipe.

Figure 8:
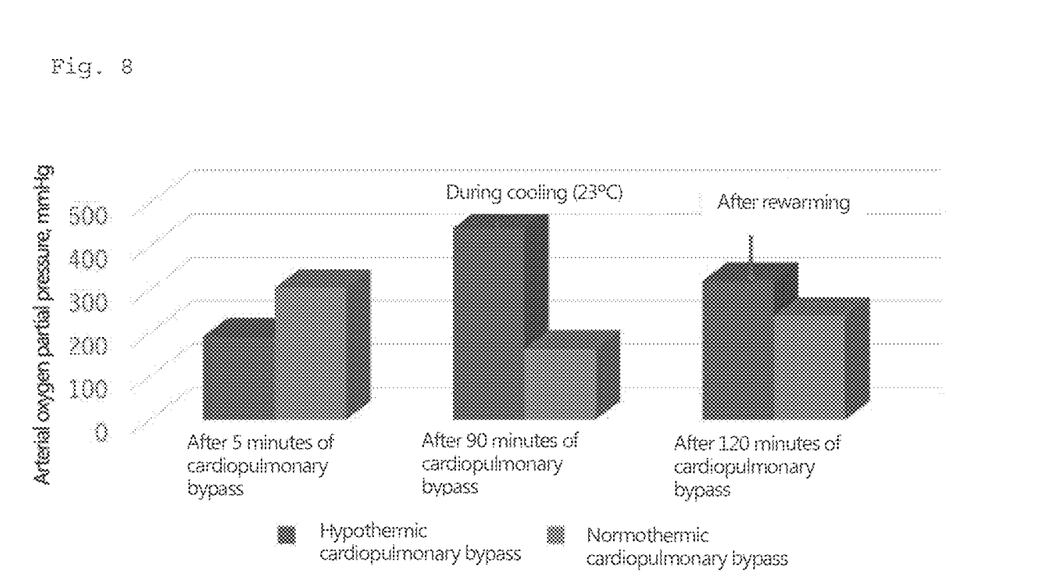
FIG. 8 shows the results (arterial oxygen partial pressure, mmHg) of an experiment of application of a cardiopulmonary bypass to pigs.

The present inventors performed a 120-minute cardiopulmonary bypass (CPB) experiment by attaching the oxygenator of the present invention to pigs. Table 3 and FIG. 8

TABLE 3

| | | CPB at deep hypothermia (23° C.) | | | CPB at normal body temperature (37° C.) | |
|---|---|---|---|---|---|---|
| | 5 minutes after the start of cardio-pulmonary bypass | Immediately before rewarming (before release of aortic clamping) | Immediately before the end of cardio-pulmonary bypass | 5 minutes after the start of cardio-pulmonary bypass | At the same time as hypothermia group (before release of aortic clamping) | Immediately before the end of cardio-pulmonary bypass |
| Core Temperature (° C.) | 35.1 ± 1.2 | 22.8 ± 0.9 | 36.7 ± 0.5 | 34.3 ± 2.2 | 35.3 ± 1.7 | 36.6 ± 0.4 |

TABLE 3-continued

| | CPB at deep hypothermia (23° C.) | | | CPB at normal body temperature (37° C.) At the same | | |
|---|---|---|---|---|---|---|
| | 5 minutes after the start of cardio-pulmonary bypass | Immediately before rewarming (before release of aortic clamping) | Immediately before the end of cardio-pulmonary bypass | 5 minutes after the start of cardio-pulmonary bypass | time as hypothermia group (before release of aortic clamping) | Immediately before the end of cardio-pulmonary bypass |
| $PO_2$ (mmHg) | 154.2 ± 120.8 | 309.0 ± 124.2 | 256.3 ± 38.8 | 243.2 ± 94.8 | 148.0 ± 96.8 | 216.0 ± 24.5 |
| Oxygen ($FiO_2$) | 0.8 ± 0.2 | 0.7 ± 0.1 | 0.8 ± 0.1 | 0.8 ± 0.2 | 0.9 ± 0.2 | 0.9 ± 0.1 |
| PF ratio | 180 ± 200 | 473 ± 200 | 325 + 72 | 333 ± 195 | 127 ± 34 | 241 ± 37 |

When the oxygenator of the present invention is used at deep hypothermia (23° C.), the PF ratio (=$PO_2$ (oxygen partial pressure)/$FiO_2$ (oxygen concentration of inhaled air)) is significantly increased to 400 or more. The results clearly show that the oxygenator of the present invention is particularly effective in therapy at deep hypothermia (20 to 25° C.) to profound hypothermia (20° C. or less).

Further, using the double-pipe oxygenator of the present invention and a conventional single-pipe oxygenator without a gas cooling part (trade name: CM-SX18H, manufactured by Terumo Corporation) and using water as a medium, the extracorporeal blood circulation was performed under the conditions described in Table 4. The amount of water vapor condensation in the entire oxygenator was measured. Table 4 shows the results. In Table 4, "%" indicates "% (v/v)".

TABLE 4

| Oxygenator | Water temperature | Water perfusion rate (L/min) | Type of gas | Gas volume (L/min) | Amount of condensation (g/sec) |
|---|---|---|---|---|---|
| Single-pipe | — | | $O_2$ 50% + He 50% | 2 | 2.831E−04 |
| Double-pipe | 4° C. | 1 | $O_2$ 50% + He 50% | 2 | 6.249E−04 |
| Double-pipe | 20° C. | 1 | $O_2$ 50% + He 50% | 2 | 2.440E−04 |
| Double-pipe | 30° C. | 1 | $O_2$ 50% + He 50% | 2 | 3.651E−06 |
| Double-pipe | 30° C. | 2 | $O_2$ 50% + He 50% | 4 | 2.300E−07 |
| Double-pipe | 35° C. | 1 | $O_2$ 50% + He 50% | 2 | 3.357E−07 |
| Double-pipe | 4° C. | 1 | He 100% | 2 | 1.045E−05 |
| Double-pipe | 4° C. | 1 | $O_2$ 50% + $N_2$ 50% | 2 | 8.840E−04 |

The above results in Table 4 show that the double-pipe oxygenator of the present invention can effectively inhibit wet lung phenomenon; that helium gas is more effective than nitrogen gas in reducing the amount of water condensation; and that when helium gas is used, the amount of condensation does not increase, even with strong cooling.

DESCRIPTION OF THE REFERENCE NUMERALS

1: Hollow fiber membrane oxygenator
2: Housing
3: Gas exchange part
4: Blood
5: Blood inlet port
6: Blood outlet port
7: Oxygen-containing gas
8: Gas inflow port
9: Gas outflow port
10: Medium
11: Medium (cold water, warm water) inlet port
12: Medium (cold water, warm water) outlet port
13: Hollow fiber membrane
14: Gas temperature control part
14a: Temperature control part
15: Partition wall (for fixing the hollow fiber membrane)
16: Partition wall (for fixing the gas temperature control part)
17: Volume control bag
18: Vented arterial filter 19: Centrifugal pump
20: Blood discharge line (venous line)
21: Blood supply line (arterial line)
22: Cooling gas (e.g., He+$O_2$)
30: Two-way cock
31: Two-way valve
32: Tube
33: Centrifugal pump
34: Temperature sensor
35: Heated saline solution
36: Cold- or warm-water tank
37: Venous reservoir

The invention claimed is:

1. A hollow fiber membrane oxygenator comprising
a housing comprising a blood flow path;
a blood inlet port and a blood outlet port disposed in the housing so as to allow blood to flow through the blood flow path, a gas exchange part comprising a bundle of a plurality of hollow fiber membranes disposed in the blood flow path;
a gas inflow port and a gas outflow port provided in the housing so as to allow an oxygen-containing gas to flow through lumens of the hollow fiber membranes;
a gas temperature control part for adjusting the temperature of the gas flowing through the lumens of the hollow fiber membranes; and
the gas temperature control part comprises cold- or warm-water flow pipes which are inserted in the hollow fiber membranes.

2. The hollow fiber membrane oxygenator according to claim 1, wherein the oxygen-containing gas further contains helium gas.

3. The hollow fiber membrane oxygenator according to claim 2, further comprising a gas separation membrane for recovering helium from gas released from the gas outflow port.

4. The hollow fiber membrane oxygenator according to claim 1, wherein the gas temperature control part selectively cools the local area inside the oxygenator where the blood and hollow fiber membranes come into contact with each other.

5. The hollow fiber membrane oxygenator according to claim 1, wherein the gas temperature control part adjusts the temperature of the oxygen-containing gas in the lumens of the hollow fiber membranes.

6. The hollow fiber membrane oxygenator according to claim 1, wherein the gas temperature control part adjusts the temperature of the gas flowing through the lumens of the hollow fiber membranes for the whole length of the lumens of the hollow fiber membranes.

7. The hollow fiber membrane oxygenator according to claim 1, wherein the hollow fiber membranes and the gas temperature control part constitute a heat exchange part, and the oxygenator is a hollow fiber membrane-based gas and heat exchanger.

8. The hollow fiber membrane oxygenator according to claim 2, wherein the hollow fiber membranes and the gas temperature control part constitute a heat exchange part, and the oxygenator is a hollow fiber membrane-based gas and heat exchanger.

* * * * *